United States Patent

Schulz et al.

[11] Patent Number: 5,834,511
[45] Date of Patent: Nov. 10, 1998

[54] DL- DI- OR TRI-HYDROXYPHENYLGLYCINE ALKYL ESTERS FOR THE TREATMENT OF INFLAMMATORY AND ALLERGIC CONDITIONS

[75] Inventors: Elisabeth Schulz; Manfred Kobow, both of Rostock; Tankred Schewe, Berlin; Wolf-Dietrich Sprung, Rostock, all of Germany

[73] Assignee: Ciba Specialty Chemicals Corporation, Tarrytown, N.Y.

[21] Appl. No.: 884,332

[22] Filed: Jun. 27, 1997

Related U.S. Application Data

[63] Continuation of Ser. No. 704,781, filed as PCT/EP95/00914, Mar. 13, 1995, published as WO95/25715, Sep. 28, 1995, abandoned.

[30] Foreign Application Priority Data

Mar. 24, 1994 [CH] Switzerland .............................. 884/94

[51] Int. Cl.⁶ .......................... A61K 31/24; C07C 205/00
[52] U.S. Cl. .............................................. 514/538; 560/23
[58] Field of Search ................................ 560/23; 514/538

[56] References Cited

FOREIGN PATENT DOCUMENTS 262 021 A1  11/1988  Germany .
262021     11/1988  Germany .

OTHER PUBLICATIONS

E. Schulz et al., vol. 32, No. 1/2, pp. 65–66 (1991).
E. Schulz et al., vol. 45, No. 12, pp. 925–928 (1990).
Schulz et al., Pharmazie 45(12), pp. 925–928, 1990.
Schulz et al., Agents and Actions, vol. 32, 1/2, pp. 65–66, 1991.

*Primary Examiner*—Raymond Henley, III
*Attorney, Agent, or Firm*—Kevin T. Mansfield

[57] ABSTRACT

The invention relates to DL-hydroxyphenylamino acid esters of formula

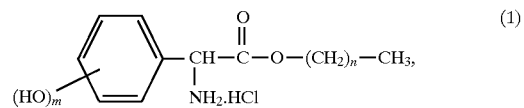

wherein
n is 3 to 12 and
m is 2 or 3.

The compounds are useful as therapeutic agents having antiinflammatory, analgesic, antiallergic and antiasthmatic properties, and also as cosmetic compositions.

10 Claims, No Drawings

DL- DI- OR TRI-HYDROXYPHENYLGLYCINE ALKYL ESTERS FOR THE TREATMENT OF INFLAMMATORY AND ALLERGIC CONDITIONS

This application is a continuation of application Ser. No. 08/704,781, filed Sep. 12, 1996, now abandoned, which is a 371 of PCT/EP95/00914 filed Mar. 13, 1996 published as WO95/25715, Sep. 28, 1995.

The present invention relates to novel DL-hydroxyphenylamino acid esters, to a process for the preparation of these compounds and to pharmaceutical compositions containing them. The invention further relates to the use of the novel compounds as therapeutic or cosmetic agents and to the use of such compounds for the preparation of medicaments for the treatment of inflammatory and allergic conditions.

It is standard practice to use glucocorticoids for the topical treatment of inflammatory and allergic conditions. It is common knowledge that these compounds can have unwanted side-effects.

Owing to their insufficient ability to penetrate the skin, non-steroidal antiinflammatory medicaments containing therapeutic agents such as ketoprofen, BW755c, piroxicam, diclofenac or indomethazin cannot effectively be applied topically, but only systemically (q.v. inter alia G. B. Kasting et al., Pharmacol. Skin., Vol.1, pp. 138–153, Karger, Basel 1987).

It is the object of this invention to provide pharmaceutical compositions having pharmacologically useful properties, in particular inflammatory, analgesic, antiallergic and antiasthmatic properties, especially when administered locally and/or by inhalation.

Surprisingly, it has been found that compounds of formula

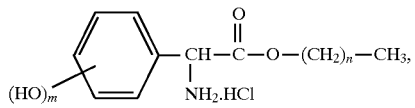

wherein n is 3 to 12 and
m is 2 or 3, exhibit marked antiinflammatory action in cellular and enzymatic in vitro assays and in in vivo assays on animals.

Those compounds of formula (1) have proved particularly interesting in which n is 3 to 9.

Compounds of very particular interest are those of formula

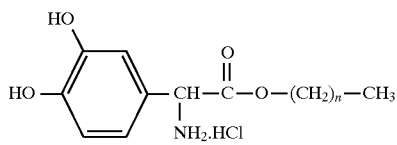

or those of formula

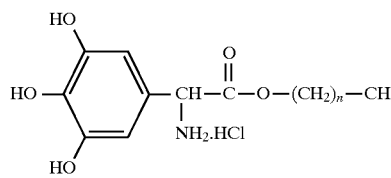

wherein n is 3 to 9.

The compounds of formula (1) are useful for the treatment of inflammatory and allergic spasmolytic conditions, as well as for the treatment of psoriasis, bronchial asthma, arteriosclerosis and conditions involving disturbances of cell proliferation.

As a function of their structure and in systemic dose-related administration, the compounds of formula (1) inhibit the paw oedema in rats induced by carrageenan (q.v. Example 14).

They are also effective when applied locally to the oedema on mice ears induced by croton oil (q.v. Example 15).

The compounds of formula (1) also have analgesic action. For example, they inhibit the writhing reactions induced in mice by i.p (=intraperitoneal) administration of acetic acid (q.v. Example 16).

It can be demonstrated that the compounds of formula (1) effect non-competitive inhibition of contractions induced by histamine, acetyl choline or barium chloride in isolated smooth muscular organs (guinea pig ileum and trachea).

In vitro assays show that the compounds of formula (1) inhibit the formation of different mediators that are an important factor in inflammation. They reduce the activities of PGH synthase as well as 5- and 15-lipoxygenase (q.v. Example 17). Furthermore, they inhibit the formation of hydrogen peroxide (cf. Example 18).

Galenic formulations comprising the compounds of formula (1) will be understood as meaning in particular emulsions, ointments, gels, sprays, powders and the like. Compounds of formula (1) may also be contained in liposomes or used in pharmacological compositions with conventional carriers and penetration enhancers, for example urea, propylene glycol, oleic acid and the like [q.v. also Barry, B. W. in: Schroot,B.; Schaefer,H. (Eds.): Pharmacol. Skin., Vol.1, pp.121, Karger, Basel 1987]. The pharmaceutical composition will usually contain the compounds of formula (1) in amounts of 0.01 to 15% by weight, preferably of 0.1 to 5% by weight, of the total mixture. For the treatment of the conditions listed hereinabove, the pharmaceutical composition of this invention may contain, in addition to the compounds of formula (1), further pharmaceutical agents having antiphlogistic activity, typically including antiinflammatory agents, antipsoriatic agents, cell proliferation regulators, and antiallergic, gastroprotective and antiasthmatic agents.

The invention further relates to a cosmetic composition comprising a compound of formula (1), together with a cosmetically acceptable carrier or adjuvant.

The compounds of formula (1) are novel. The process for their preparation is also an object of the invention (Examples 1 and 2). The process comprises reacting the amino acid of formula

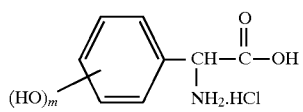

with an alcohol of formula

in the presence of thionyl chloride, to compounds of formula (1). In formulae (4) and (5)

m is 2 or 3, and n is 3 to 12.

The reaction time is from 2 to 10, preferably from 2.5 to 5, hours. The reaction temperature is conveniently in the range from 60° to 80°, preferably from 75° to 80° C.

The general reaction of DL-phenylamino acids with alcohols in the presence of thionyl chloride is described in Pharmazie 47, 55 (1992).

The following Examples will serve to illustrate the invention without implying any restriction to what is described therein. Unless otherwise indicated, percentages are by weight.

A. Preparation of the novel compounds

EXAMPLE 1

Preparation of DL-3,4-dihydroxyphenylglycine octyl ester hydrochloride

With stirring, 9.52 g (0.08 mol) of thionyl chloride are added dropwise to a suspension of 9.16 g (0.05 mol) of DL-3,4-dihydroxyphenylglycine and 97.7 g (0.75 mol) of n-octyl alcohol. The mixture is heated for 3 hours to 80° C. and then cooled. A further 3.57 g (0.03 mol) of thionyl chloride are added and the reaction mixture is again heated for 1 hour to 80° C. The solvent is removed under vacuum and, for purification, the residue is taken up in 150 ml of a saturated solution of $(NH_4)_2CO_3$ and extracted with 2×100 ml of diethyl ether. The combined ethereal extract is dried over sodium sulfate and filtered. Dry HCl is then passed through the filtrate. The precipitate is isolated by filtration and recrystallised from a mixture of n-propanol/diethyl ether, affording 4.15 g (yield: 25% of theory) of the compound of formula

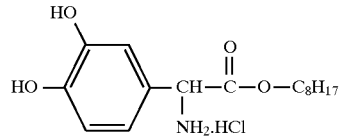

Elemental analysis:

|        | C     | H    | N    |
|--------|-------|------|------|
| clcd:  | 57.91 | 7.90 | 4.22 |
| found: | 57.57 | 7.72 | 4.26 |

EXAMPLE 2

The procedure of Example 1 is repeated, but replacing 0.05 mol of DL-3,4-dihydroxyphenylglycine with 0.05 mol of DL-3,4,5-trihydroxyphenylglycine, giving 6.44 g (yield: 37% of theory) of the compound of formula

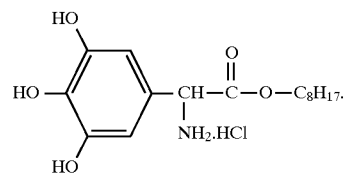

Elemental analysis:

|        | C     | H    | N    |
|--------|-------|------|------|
| clcd:  | 55.25 | 7.53 | 4.03 |
| found: | 55.21 | 8.03 | 3.95 |

EXAMPLES 3 to 5

The procedure of Example 1 is repeated, but replacing 0.75 mol of n-octyl alcohol by -n-nonylalkonhol (Example 3), -n-decylalkonhol (Example 4), and -n-dodecylalkonhol (Example 5).

Compounds of the formulae (103)–(106)

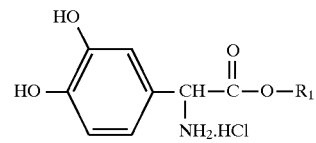

(103): $R_1$ n-nonyl (104): $R_1$ n-decyl (105): $R_1$ n-dodecyl are obtained.

B. Preparation of pharmaceutical and cosmetic compositions

EXAMPLE 6

An ointment containing 2% of the compound of formula (102) can be prepared as follows:

Composition:

active ingredient 2% vaseline 45.0% paraffin oil 19.6% cetyl alcohol 5.00% beeswax 5.00% sorbitan sesquioleate 5.00% p-hydroxybenzoate 0.20% demineralised water to make up 100.00%

The fatty substances and emulsifiers are fused together and the active ingredient is dissolved therein. The preservative is dissolved in water and the solution is emulsified at elevated temperature into the melt and the emulsion is then stirred until cold.

EXAMPLE 7

A cream containing 1% of the compound of formula (101) can be prepared as follows:

Composition:

active ingredient 1% isopropyl palmitate 8.0% cetyl palmitate 1.5% silicone oil 100 0.5% sorbitan monostearate 3.0% polysorbate 60 3.5%

1,2-propylene glycol PH 20.0% acrylic acid polymer 0.5% triethanolamine 0.7% demineralised water to make up 100.00%

The acrylic acid polymer is suspended in a mixture of demineralised water and 1,2-propylene glycol. With stirring, triethanolamine is added to form a mucilage. A mixture of isopropyl palmitate, cetyl palmitate, silicone oil, sorbitan monostearate and polysorbate is heated to c. 75° C. and the active ingredient is dissolved therein. This fatty phase is stirred into the mucilage, which is also heated to c. 75° C., and the batch is stirred until cold.

EXAMPLE 8

A cream containing 0.5% of the compound of formula (102) can be prepared as follows:

Composition:

active ingredient 0.5% cetyl palmitate PH 2.00% cetyl alcohol PH 2.00% triglyceride mixture of saturated medium fatty acids 5.00% stearic acid 3.00% glycerol stearate PH 4.00%

Cetomacrogol 1000 1.00% microcrystalline cellulose 0.50%

1,2-propylene glycol, dist. 20.00% demineralised water to make up 100.00%.

Cetyl alcohol, cetyl palmitate, the triglyceride mixture, stearic acid and glycerol stearate are fused together and the active ingredient is dissolved therein. The microcrystalline cellulose is dispersed in some of the water. Cetomacrogol is dissolved in the remainder of the water and the propylene glycol and the mucilage are mixed therewith. The fatty phase is then stirred into the aqueous phase and stirred until cold.

The formulation is suitable for use as a moisturising skin-protective cream.

EXAMPLE 9

A transparent hydrogel containing 0.2% of the compound of formula (102) is prepared as follows:

Composition:

active ingredient 0.2% propylene glycol 10.0–20.0% isopropanol 20.0% hydroxypropylmethyl cellulose 2.0% water to make up 100.00%

The hydroxypropylmethyl cellulose is swollen in water. The active ingredient is dissolved in a mixture of isopropanol and propylene glycol. Then the active ingredient solution is mixed with a swollen cellulose derivative and, if desired, perfume is added (0.1%).

The formulation is suitable for use as a moisturising skin gel.

EXAMPLE 10

A transparent hydrogel containing 0.02% of the compound of formula (102) is prepared as follows:

Composition:

active ingredient 0.02% propylene glycol 20.0% isopropanol 20.0% acrylic acid polymer 2.0% triethanolamine 3.0% water to make up 100.00%

Acrylic acid polymer and water are dispersed and the dispersion is neutralised with triethanolamine. The active ingredient is dissolved in a mixture of isopropanol and propylene glycol. The active ingredient solution is then mixed with a gel and, if desired, perfume oil (0.1%) can be added.

EXAMPLE 11

A foam spray containing 1% of the compound of formula (102) can be prepared as follows:

Composition:

active ingredient 1% cetyl alcohol PH 1.70% viscous paraffin oil 1.00% isopropyl myristate 2.00%

Cetomacrogol 1000 2.40% sorbitan monostearate 1.50%

1,2-propylene glycol PH 5.00% methyl parabene 0.18% propyl parabene 0.02%

Chemoderm 314 0.10% demineralised water to make up 100.00%

Cetyl alcohol, paraffin oil, isopropyl myristate, Cetomacrogol and sorbitan stearate are fused together and the active ingredient is dissolved therein. Methyl and propyl parabene are dissolved in propylene glycol and the solution is added to the hot water. The melt and the solution are afterwards mixed. After cooling, the Chemoderm is added and, if desired, perfume oil (0.1%) the formulation is bulked with water to the final weight.

Filling:

An aluminium dispenser is filled with 20 ml of the mixture. The dispenser is fitted with a nozzle and propellant gas is introduced under pressure.

EXAMPLE 12

An eye ointment containing 0.01% of the compound of formula (101) can be prepared as follows:

Composition:

active ingredient 0.01% viscous paraffin oil 10% wool grease anhyd. 10% white vaseline 79%

100%

The constituents are fused together and filtered under sterile conditions.

EXAMPLE 13

Capsules suitable for insufflation and containing 0.025% of the compound of formula (102) can be prepared as follows:

Composition: (for 1000 capsules)
active ingredient 25.00 g
milled lactose 25.00 g The active ingredient and the microfine lactose are thoroughly blended. The powder is sieved and filled in 0.05 g portions into gelatine capsules.

C: Use Examples

EXAMPLE 14

Action on the carrageenan oedema after systemic application

The DL-phenylarnino acid ester prepared in Examples 1 and 2 is assayed for its activity in male and female Wistar rats ((100–150 g, 8 animals per group). The oedema is induced by subplantar injection of 0.1 ml of a 1% solution of carrageenan (viscarin®) into both hind paws of the rats. The compounds of formulae (101) and (102) are administered simultaneously i.p. The paw diameters are measured before and 3 hours after inducing the oedema. The percentage inhibition of the paw swelling is determined by comparison with the control group. The following $ED_{50}$ values (ED=effective dose) are found by linear regression (Table 1):

Table 1

|  | $ED_{50}[10^{-4}$ mol/kg] |
|---|---|
| compound of formula (101) | 1.5 |
| compound of formula (102) | 0.8 |
| acetylsalicylic acid*) | 15.2 |

*)comparison substance

EXAMPLE 15

Antioedamatous activity

The assays for determining the antioedamatous activity of the novel compounds of formulae (101) and (102) prepared in Examples 1 and 2 are carried out on male AB mice (18–22 g, 9 animals per group). The ear oedema is induced by applying 2×10 μl of croton oil (1% in acetone) to the ears of the mice. After 1 hour the novel compounds (2×10 μl of a 5% ethanolic solution of each compound) are applied. After a further 5 hours (6 hours after inducing oedema) the animals are sacrificed, and pieces of ear tissue having a diameter of 8 mm are obtained. The oedema weight is determined as the difference between the contralateral ear. The percentage inhibition is calculated from a comparison with the control animals. (Table 2).

TABLE 2

|  | Inhibition [%] |
|---|---|
| compound of formula (101) | 23.9 |
| compound of formula (102) | 45.7 |

EXAMPLE 16

Activity against the writhing syndrome

The activity of the novel compounds of formulae (101) and (102) against the writhing syndrome is carried out on female CBA mice (c. 20 g, 9 animals per group). The writhing reactions are induced by i.p. (=intraperitoneal) injection of 0.1 ml of 1% acetic acid/10 g and recorded over a period of 20 minutes after injection. The compounds of formulae (101) and (102) are administered i.p. in a dose of $5 \times 10^{-5}$ mol/kg 30 minutes before inducement of the writhing reactions, and the percentage inhibition of the number of reactions is determined (Table 3).

TABLE 3

|  | Inhibition [%] |
|---|---|
| compound of formula (101) | 80.2 |
| compound of formula (102) | 80.7 |
| acetylsalicylic acid*) | 32.3 |

*)comparison substance

EXAMPLE 17

Inhibition of arachidonic acid metabolism

Prostaglandin H synthase is prepared from the seminal vesicles of sheep (F. S. Van der Ouderaa, M. Buytenhek.: Methods Enzymol. 86, 60–68 (1982)), and 15-lipoxygenase from rabbit reticulocytes (T. Schewe, R. Wiesner, S. M. Rapoport: Methods Enzymol. 71, 430–441 (1981)). Both enzymatic activities are measured oxygraphically at 25° C.

The prostaglandin H synthase activity is determined in 0.1 molar tris-HCl at pH 8.0 containing 0.1 μmol/l of EDTA-Na, and 0.5 μmol of phenol, using microsomal enzyme preparations with 30 μmol/l of arachidonic acid as substrate (Ch. Schewe, P. Ludwig, H. G. Holzhütter, T. Schewe: Pharmazie 46, 804–809 (1991)).

The 15-lipoxygenase activity is measured using 265 μmol/l of potassium linoleate as substrate in 0.1 molar phosphate puffer at pH 7.4 and 0.2% sodium cholate (T. Schewe, H. Kühn, S. M. Rapoport, in: Prostaglandins and Related Substances—A Practical Approach pp. 229–242, C. Benedetto, R. G. McDonald-Gibson, S. Nigam, T. F. Slater (Eds.); IRL Press, Oxford, Wash. (1987)). The compounds are freshly dissolved in 2-methoxyethanol and preincubated for 5 minutes with the enzyme preparation, and the reaction is started by addition of substrate.

The influence of the formation of 5-HETE by 5-lipoxygenase of human polymorphonuclear leucozytes from 1-$^{14}$C-arachidonic acid (10 μmol/l) by the compounds is determined, after thin-layer chromatographic separation, by the radioactive distribution of the reaction products (Table 4) (Ch. Schewe, E. Schulz, G. Vietinghoff, W. -D. Sprung, M. Kobow, S. Loose, T. Schewe: Biomed.Biochim.Acta 50, 189–198 (1991)).

TABLE 4

|  | PGH Synthase $IC_{50}$ $10^{-6}$mol/l | 5-LOX $IC_{50}$ $10^{-6}$mol/l | 5-HETE formation $IC_{50}$ $10^{-6}$mol/l |
|---|---|---|---|
| compound of formula (101) | 110 | 3.9 | 6.9 |
| compound of formula (102) | 85 | 250 | 1.3 |
| acetylsalicylic acid*) | 50 | >1000 | — |

*)comparison substance
IC = inhibitory concentration

EXAMPLE 18

Inhibition of hydrogen peroxide formation

The influence of the novel compounds of formulae (101) and (102) on the formation of hydrogen peroxide induced by opsonated zymosan is determined using casein-stimulated peritoneal granulocytes of rats ($5 \times 10^6$ cells/ml). In this assay, the oxidation of phenol red induced by $H_2O_2$ is measured from the absorption at 610 nm (E. Pick, Y. Keisari:

J. Immunol.Meth. 38, 161–170 (1980)). After an incubation time of 30 min the percentage inhibition of the formation of hydrogen peroxide and the $IC_{50}$ is computed by means of linear regression (Table 5).

TABLE 5

|   | $IC_{50}$ [$10^{-6}$mol/l] |
|---|---|
| compound of formula (101) | 2.3 |
| compound of formula (102) | 5.3 |
| acetylsalicylic acid*) | >100 |

*)comparison substance

What is claimed is:

1. A compound of formula

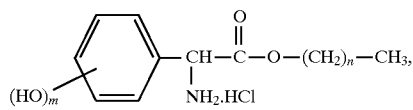   (1)

wherein n is 3 to 12 and m is 2 or 3.

2. A compound according to claim 1, wherein n is 3 to 9.

3. A compound according to claim 2 of formula

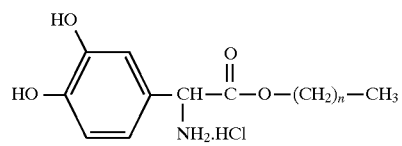   (2)

wherein n is 3 to 9.

4. A compound according to claim 2 of formula

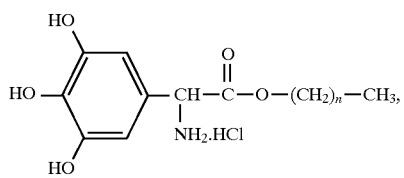   (3)

wherein n is 3 to 9.

5. A pharmaceutical composition comprising a pharmaceutically effective amount of a compound as claimed in claim 1, together with a pharmaceutically acceptable carrier or adjuvant.

6. A pharmaceutical composition according to claim 5, which additionally comprises at least one substance having antiphlogistic action.

7. A cosmetic composition comprising a cosmetically effective amount of a compound as claimed in claim 1, together with a cosmetically acceptable carrier or adjuvant.

8. A process for the preparation of a compound of formula

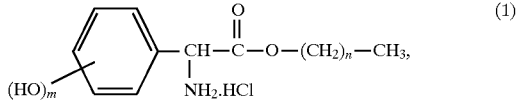   (1)

which comprises reacting the amino acid of formula

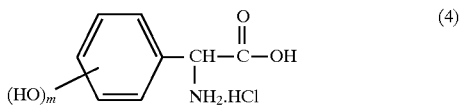   (4)

with an alcohol of formula

   (5)

in the presence of thionyl chloride, to compounds of formula (1) wherein, in formulae (1), (4) and (5)

m is 2 or 3, and n is 3 to 12.

9. A method for the topical and/or inhalational treatment of inflammatory and allergic conditions, which comprises administration of a pharmaceutical composition according to claim 5 to a patient in need of such treatment.

10. A method for the preparation of a medicament for the treatment of inflammatory and allergic spasmolytic conditions, as well as for the treatment of psoriasis, bronchial asthma, arteriosclerosis and conditions involving disturbances of cell proliferation, which comprises incorporating a pharmaceutically effective amount of a compound according to claim 1 into said medicament.

* * * * *